US012582366B2

(12) United States Patent
Sarkar

(10) Patent No.: US 12,582,366 B2
(45) Date of Patent: Mar. 24, 2026

(54) ROBOTIC TRANSFER DEVICE AND RELATED METHOD

(71) Applicant: Pritam Kumar Sarkar, Toronto (CA)

(72) Inventor: Pritam Kumar Sarkar, Toronto (CA)

( * ) Notice: Subject to any disclaimer, the term of this patent is extended or adjusted under 35 U.S.C. 154(b) by 239 days.

(21) Appl. No.: 18/098,623

(22) Filed: Jan. 18, 2023

(65) Prior Publication Data

US 2023/0301608 A1     Sep. 28, 2023

Related U.S. Application Data

(60) Provisional application No. 63/307,132, filed on Feb. 6, 2022.

(51) Int. Cl.
*A61B 6/04*          (2006.01)
*A61G 13/02*          (2006.01)

(52) U.S. Cl.
CPC ............ *A61B 6/0487* (2020.08); *A61G 13/02* (2013.01); *A61B 6/0407* (2013.01)

(58) Field of Classification Search
CPC ..... A61B 6/0487; A61B 6/0407; A61B 6/032; A61B 6/037; A61B 6/547; A61B 6/08; A61B 6/4441; A61B 5/06; A61B 5/064; A61B 6/0414; A61B 5/1127; A61G 13/02; A61G 7/1019; A61G 7/1034; A61G 7/1048; A61G 7/1057; A61G 2203/22; A61G 2203/32; A61G 2203/40; A61G 2203/72; A61G 1/0237; A61G 1/0275; A61G 1/0225; A61G 13/06; A61G 2203/10; A61G 7/08; A61G 5/04; A61G 1/0287; A61G 1/0281; A61G 7/0528; A61G 7/05; A61G 7/103; A61G 7/0527; A61G 13/08; A61G 13/104; A61G 2203/44; A61G 2205/60;
(Continued)

(56) References Cited

U.S. PATENT DOCUMENTS 3,854,152 A * 12/1974 Chez .................... A61G 7/1019
                                                              5/81.1 C
4,369,533 A * 1/1983 Gisiger ................. A61G 7/001
                                                              5/607
(Continued)

FOREIGN PATENT DOCUMENTS

CN      201620736399.4 U      3/2016
CN      201820733896.8 U      1/2019
(Continued)

*Primary Examiner* — Madison Emanski

(57)                ABSTRACT

A robotic transfer device is an unmanned vehicle carrying an articulated body that can load, unload, and transport a payload. The configuration of the articulated body is such that one of the degrees of freedom is along a vertical axis so that it can lift a payload from the bottom. At the tip, the articulated body has a roller bed which can be moved up or down with or without a payload. When the rollers rotate about their own axes, the payload moves linearly along the direction of motion perpendicular to the axis of rotation. This phenomenon helps transporting the payload from one robotic transfer device to another. If a patient bed is detachable from the frame, then the robotic transfer device can lift the bed along with the patient. A robotic transfer device and a method of transferring patient from one robotic transfer device to another are disclosed.

18 Claims, 11 Drawing Sheets

(58) Field of Classification Search
CPC ........ A61G 7/012; A61G 7/002; A61G 7/065;
A61G 13/0018; A61G 7/015; A61G
13/04; A61G 2210/50; A61G 7/1026;
A61G 7/1036; A61G 2200/32; A61G
7/1032; A61G 2200/34; A61G 7/1046
USPC ............. 5/81.1 C, 81.1 R, 81.1 HS; 198/321
See application file for complete search history.

(56) References Cited

U.S. PATENT DOCUMENTS

| | | | | |
|---|---|---|---|---|
| 4,873,732 | A * | 10/1989 | Perez | .................... A61G 7/1019 |
| | | | | 5/81.1 HS |
| 5,937,456 | A * | 8/1999 | Norris | .................. A61G 7/1019 |
| | | | | 5/81.1 R |
| 7,484,252 | B2 | 2/2009 | Wang | |
| 7,571,498 | B2 | 8/2009 | Jewell | |
| 7,578,011 | B2 * | 8/2009 | Johnson | ............... A61G 7/1065 |
| | | | | 5/81.1 R |
| 9,463,127 | B2 * | 10/2016 | Hochman | ............ A61G 7/1057 |
| 10,624,805 | B2 | 4/2020 | Mahjoubi | |
| 11,052,008 | B2 | 7/2021 | Lim et al. | |
| 11,083,657 | B2 | 8/2021 | Dalbert | |
| 11,206,996 | B2 | 12/2021 | Coppens et al. | |
| 2013/0269101 | A1 * | 10/2013 | White | .................. A61G 7/1026 |
| | | | | 5/81.1 C |
| 2014/0123384 | A1 * | 5/2014 | White | .................. A61G 7/1032 |
| | | | | 156/60 |
| 2024/0065908 | A1 * | 2/2024 | Bui | ............................ A61L 2/10 |

FOREIGN PATENT DOCUMENTS

| | | | | |
|---|---|---|---|---|
| CN | 201911210336.X | | 2/2020 | |
| EP | 0453547 | B1 * | 6/1995 | ........... A61G 7/1026 |
| EP | 01810407 | B1 | 1/2002 | |
| EP | 09168488 | B1 | 8/2009 | |
| WO | 213408 | | 4/2021 | |
| WO | 213406 | | 10/2021 | |
| WO | WO-2022005161 | A1 * | 1/2022 | ............... A61G 7/02 |
| WO | WO-2022150915 | A1 * | 7/2022 | ............... A61G 7/08 |

* cited by examiner $180_1$     $180_2$     $180_3$     $180_4$     $180_5$     $180_6$     $180_7$     $180_8$

ROBOTIC TRANSFER DEVICE AND RELATED METHOD

FIELD

This application is related to the field of moving and/or transporting a payload by a robotic device, especially patient in a nursing home or hospital environment.

INTRODUCTION

Moving heavy payload from one place to another in a warehouse, hospital or other kinds of environment often requires several personnel who physically lift the payload. This task needs considerable strength and occasionally a source of injury to the personnel. While some improvement has been taking place recently in warehouse due to large scale of introduction of semi-automatic or robotic system, no change is happening in hospital. Patients are still being moved by nurses or attendants. Use of robotic transfer device in this environment not only eliminates human intervention but will safely maneuver the patient as well avoiding potential injury to the attendants.

SUMMARY

In one aspect, a robotic transfer device for lifting and transferring a payload is provided. The robotic transfer device may comprise a rolling bed, and an articulated body. The articulated body may be coupled to the rolling bed and mountable to the ground or any static object, the articulated body having one or more actuators that collectively move the rolling bed into contact with surfaces of the payload. The one or more actuators, when activated, may collectively rotate the rolling bed relative to the ground or any static object about third axis, and translate the rolling bed relative to the ground/static object along first, second and third axes.

In another aspect, a method of robotically lifting a payload is provided. The method may comprise using an algorithm that computes the path of the rolling bed to make contact with the payload avoiding obstacle, driving the rolling bed to the payload and then lifting the payload from the bottom to a certain predetermined height. The payload may be transferred thereafter to any other device or another robotic transfer device by actuating the rollers of the first robotic transfer device.

In another aspect, a robotic transfer device for lifting and transferring a payload is provided. The robotic transfer device may comprise a rolling bed, an articulated body and an unmanned vehicle. The articulated body may be coupled to the rolling bed and is mountable to the unmanned vehicle which may have one or more actuators that collectively move the unmanned vehicle along with the mounted articulated body on the ground. The one or more actuators, when activated, collectively rotate the unmanned vehicle about a vertical axis and translate along a longitudinal and transverse axis relative to any point on the ground. The articulated body may also have one or more actuators that collectively move the rolling bed into contact with surfaces of the payload. The one or more actuators, when activated, may collectively rotate the rolling bed relative to the unmanned vehicle about third axis, and translate the rolling bed relative to the unmanned vehicle along first, second and third axes.

In another aspect, a method of robotically transferring a payload using two robotic transfer devices is provided. The method may comprise using an algorithm that computes the path of the first unmanned vehicle to move to a place where from the payload is accessible from the bottom, driving the first unmanned vehicle to that place avoiding obstacle, using an algorithm that computes the path of the rolling bed to make contact with the payload avoiding obstacle, driving the rolling bed to make contact with the payload and then lifting the payload to a certain predetermined height. The method may also comprise using an algorithm that computes the path of the second unmanned vehicle to move to a place where from the payload is transferrable to the second robotic device, driving the second unmanned vehicle to that place avoiding obstacle, using an algorithm that computes the path of the second rolling bed to raise the height of the second rolling bed to the height of the first rolling bed, driving the rolling bed to the said height. Now the actuators of both roller beds are activated in a direction that guarantees the movement of the payload from first robotic transfer device to the second robotic device.

DRAWINGS

DESCRIPTION OF VARIOUS EMBODIMENTS

Numerous embodiments are described in this application and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", or "fastened" where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. As used herein, two or more parts are said to be "rigidly coupled", "rigidly connected", "rigidly attached", or "rigidly fastened" where the parts are coupled so as to move as one while maintaining a constant orientation relative to each other. None of the terms "coupled", "connected", "attached", and "fastened" distinguish the manner in which two or more parts are joined together.

As used herein and in the claims, a first element is said to be "received" in a second element where at least a portion of the first element is received in the second element unless specifically stated otherwise.

Further, although method steps may be described (in the disclosure and/or in the claims) in a sequential order, such methods may be configured to work in alternate orders. In other words, any sequence or order of steps that may be described does not necessarily indicate a requirement that the steps be performed in that order. The steps of methods described herein may be performed in any order that is practical. Further, some steps may be performed simultaneously.

Figure 1:
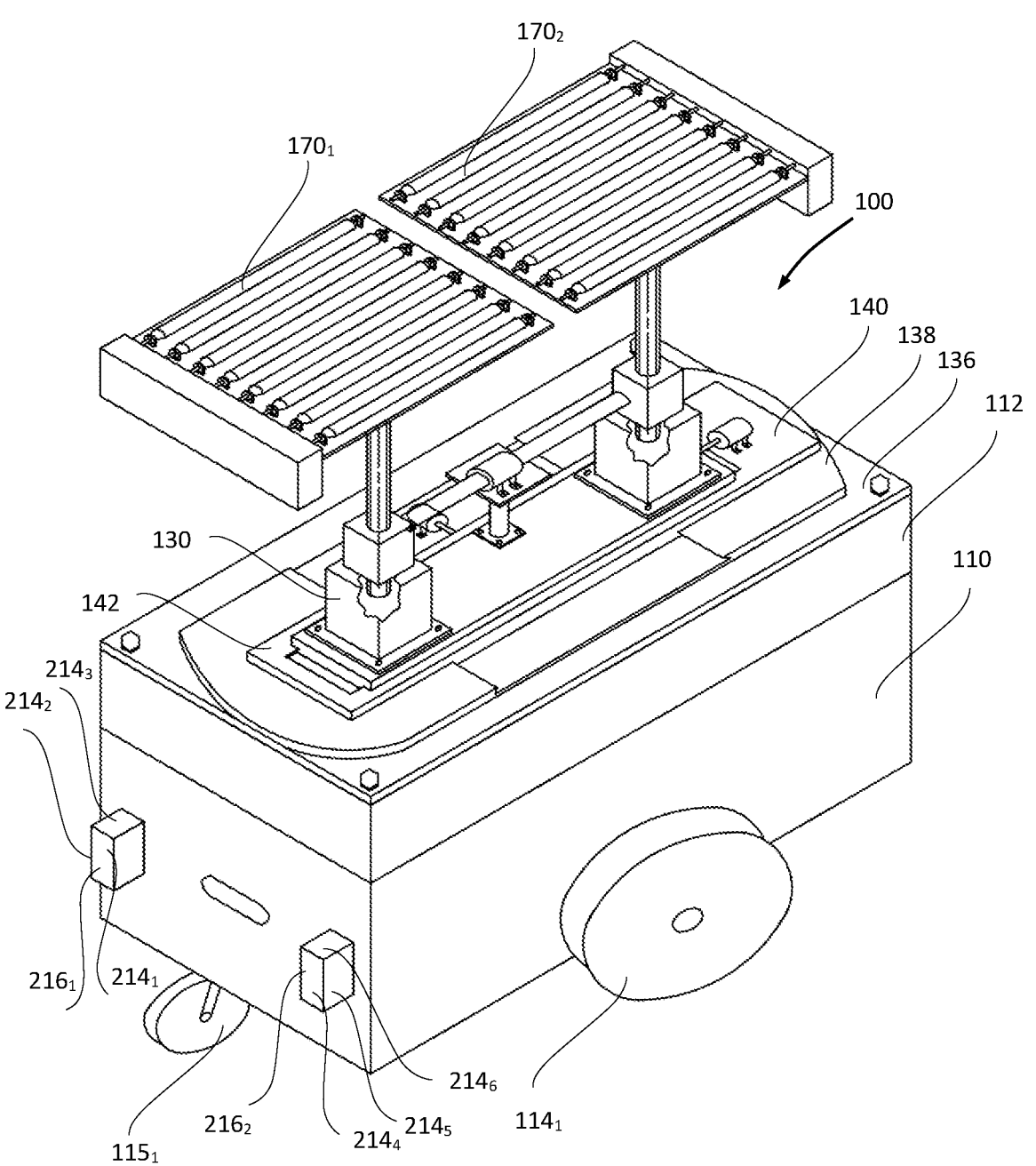
FIG. 1 is a perspective view of a robotic transfer device in accordance with an embodiment.

FIG. 1 shows a robotic transfer device 100, which is operable both manually and automatically to move and may lift a payload 200 (shown in FIG. 8), approaching payload 200 from the bottom of said payload 200. For example, robotic transfer device 100 may be operable at least to efficiently loading, unloading, transferring and transporting payload 200, as shown, from facilities to facilities. Payload 200 may be any payload such as a weight, a platform, a platform with patient, a bed, or a bed with patient. Robotic transfer device 100, when in autonomous mode, operates autonomously without any manual intervention. Robotic transfer device 100 may include an articulated body 130 that may be secured to a static or moving object. For example, articulated body 130 is secured to an unmanned vehicle 110 by a mount 112 as shown. The other end of articulated body 130 which is free to move is connected to a rolling bed 170. Articulated body 130 may be operable to move rolling bed 170 with several degrees of freedom into surface contact with payload 200. Once activated, robotic transfer device 100 may position itself under payload 200, lift payload 200 from beneath automatically (i.e. without further user action) and then, transport payload 200 to another facility, or transfer payload 200 to another robotic transfer device 100 that transport payload 200 to another facility.

Still referring to FIG. 1, robotic transfer device 100 may include an unmanned vehicle 110 that is operable to move manually. Unmanned vehicle 110 may also move or rotate autonomously from place to place on any floor or ground. For example, unmanned vehicle 110 may move on a combination of wheels 114 and castor wheels 115 along a straight line, a curvilinear or a more complex path. When the velocities of two wheels $114_1$ and $114_2$ are same both in magnitude and direction unmanned vehicle 110 moves along a straight line. However, when the velocities of two wheels $114_1$ and $114_2$ are same in magnitude but opposite in direction unmanned vehicle 110 rotates about its central vertical axis. This central vertical axis lies at the center of the line joining the centers of the two wheels $114_1$ and $114_2$ and is perpendicular to the said line joining the centers of the two wheels $114_1$ and $114_2$. When the velocities of the two wheels $114_1$ and $114_2$ are same in direction but different in magnitude unmanned vehicle 110 moves along a curvilinear path. Front Castor wheel $115_1$ and back castor wheel $115_2$ are free wheels that can rotate about their respective vertical axes. There are no actuators to drive castor wheel(s) 115.

Figure 2:
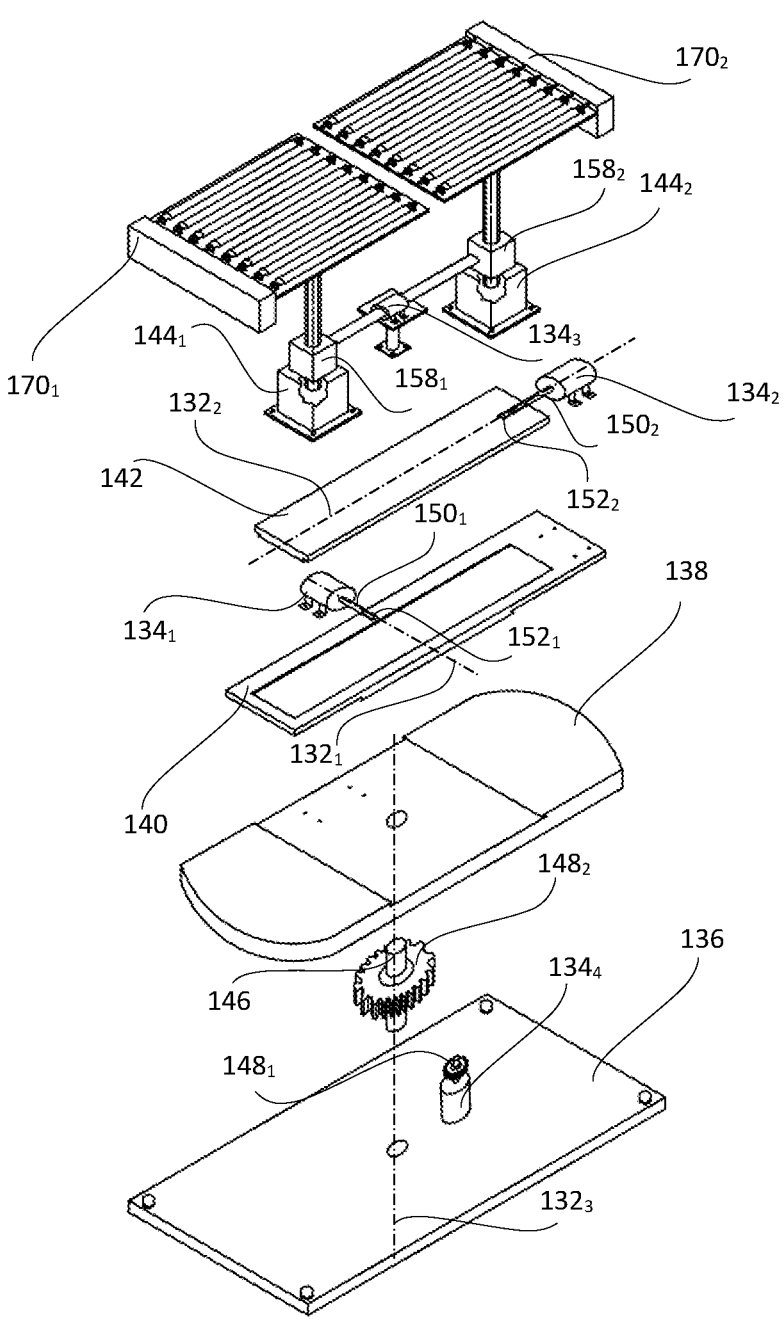
FIG. 2 is an exploded view of an articulated body.

FIG. 2 is an exploded view of articulated body 130. Articulated body 130 may include one or more actuators 134 that, when activated, collectively act to move rolling bed 170 relative to first body portion 136, the base of articulated body 130. For example, actuators(s) 134 may form part of articulated body 130 as shown. Actuators 134 may act to impart any movement upon rolling bed 170. For example, each actuator 134 may act to rotate rolling bed 170, translate rolling bed 170, or move rolling bed 170 in more complex patterns involving both rotation and translation in one or more direction. In some embodiments, actuator(s) 134 may be operable to rotate rolling bed 170 about third or yaw axis $132_3$ and translate rolling bed 170 along first, second and third axes $132_1$, $132_2$ and $132_3$. This may be achieved by any number of actuators 134.

Still referring to FIG. 2, articulated body 130 may include a first actuator $134_1$ that acts upon a screw $150_1$ and a nut $152_1$ mechanism to translate the rolling bed 170 along a first axis $132_1$, a second actuator $134_2$ that acts upon a screw $150_2$ and a nut $152_2$ mechanism to translate the rolling bed 170 along a second axis $132_2$, a third actuator $134_3$ that acts upon a screw jack(s) 158 to change the motion from a horizontal axis to a vertical axis and then acts upon an inter thread to translate the rolling bed 170 along a third axis $132_3$ and a fourth actuator $134_4$ that acts upon a first gear $148_1$ and a second gear $148_2$ to rotate the rolling bed 170 about the third axis $132_3$. Third axis $132_3$ is a vertical axis, also known as yaw axis. First and second axes $132_1$ and $132_2$ are any axes that are mutually perpendicular, but they do not lie on a same plane. So, they do not intersect with each other. Again, third axis $132_3$ is perpendicular to both first and second axes $132_1$ and $132_2$. However, first, second and third axes $132_1$, $132_2$ and $132_3$ are not collinear. While the design of articulated body 130 is primarily based on a configuration of robotic system having four degrees of freedom, other robotic configuration with one or more degree(s) of freedom can also perform the job. For example, only third axis motion may solve the problem with less flexibility to position rolling bed 170 under payload 200, or the rotation about the third axis of the above-described articulated body 130 may be designed at each of rolling bed(s) 170 to increase the flexibility of positioning rolling bed 170 under payload 200.

Figure 3:
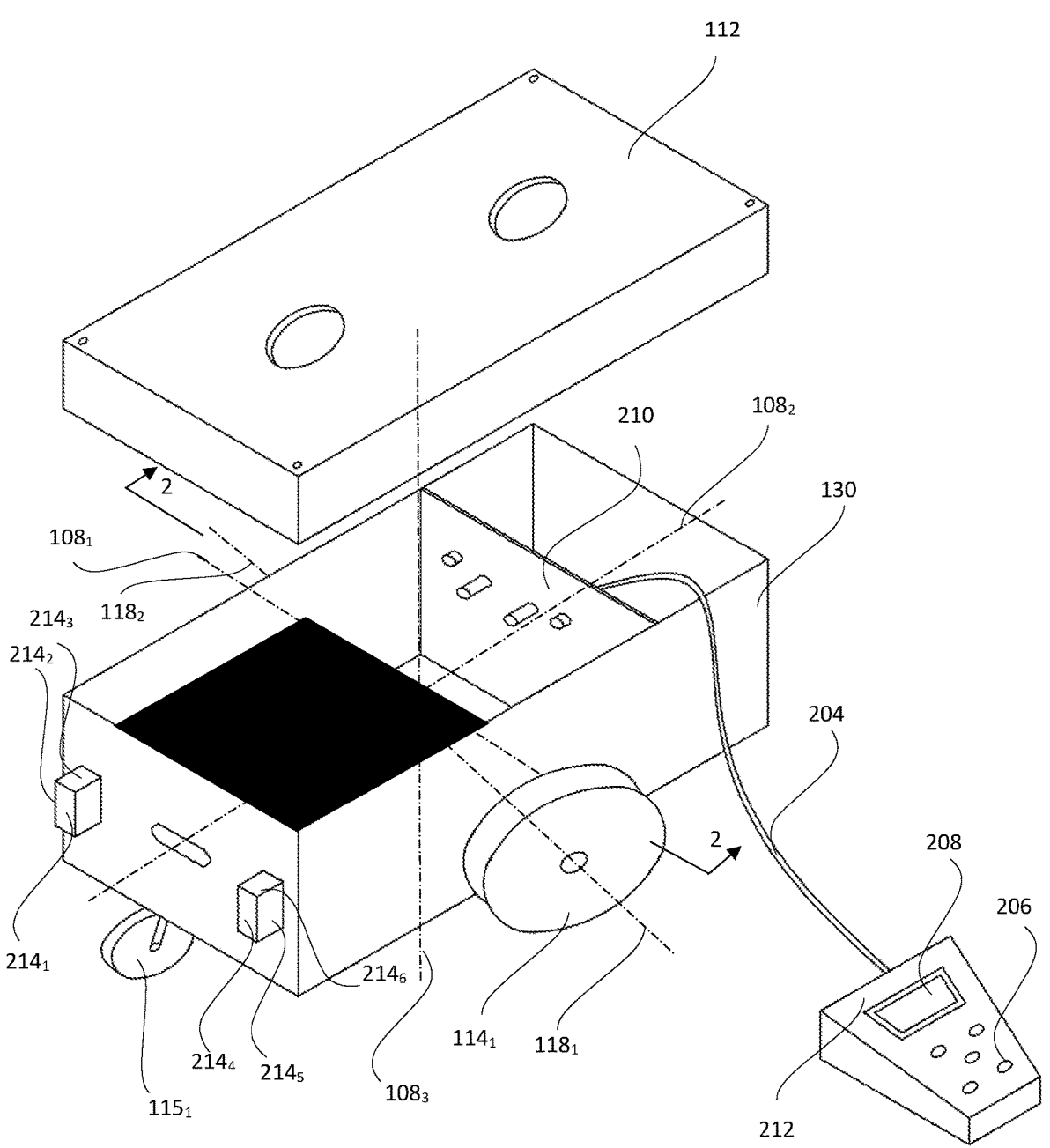
FIG. 3 is an exploded view of an unmanned vehicle.

Referring to FIG. 2-3, robotic transfer device 100 may include a controller 210 that is communicatively couple to actuator(s) 134 to send control signals that activate actuator(s) 134 automatically to perform a task defined by the user. Actuator(s) 134 can be any device that acts to impart movement upon rolling bed 170 in response to control signals (e.g. electrical signals) from controller 210. For example, actuator(s) 134 may include servos as shown, DC or AC motors, fluid piston cylinders, or another type of actuator. In the illustrated example as shown in FIG. 2, articulated body 130 includes a first body portion 136 rotatably connected about third axis $132_3$ to a second body portion 138, a third body portion 140 linearly movable along first axis $132_1$ connected to second body portion 138 and a fourth body portion 142 linearly movable along second axis $132_2$ connected to third body portion 140. As shown, fourth actuator $134_4$ may be mounted to first body portion 136 so that fourth actuator $134_4$ can be activated to impart rotation of second body portion $138$ relative to first body portion $136$ about third axis $132_3$. The motion from fourth actuator $134_4$ to second body portion $138$ is transmitted through gear $148$. Gear $148$ may be any gear that can transmit motion between coplanar parallel axes. While gear $148_1$ picks up rotary motion from an extension shaft of fourth actuator $134_4$, gear $148_2$ impart motion through shaft $146$ connected to second body portion $138$. First actuator $134_1$ may be mounted on second body portion $138$ so that first actuator $134_1$ can be activated to impart rotation onto screw $150_1$ rotatably connected about first axis $132_1$ to third body portion $140$. Third body portion $140$ is bevel shaped and may include a nut $152_1$. Third body portion $140$ is fitted into bevel shaped slot on second body portion $138$. Screw $150_1$ is connected to nut $152_1$. This arrangement, when first actuator $134_1$ drives screw $150_1$ to rotate, allows third body portion $140$ to slide smoothly on second body portion $138$ as the bevel shape restricts rotary motion of third body portion $140$. In this way, rotary motion of screw $150_1$ drivingly connected to third body portion $140$ converts rotary to linear motion resulting in third body portion $140$ to move between a retracted and an extended position. Second actuator $134_2$ may be mounted on third body portion $140$ so that second actuator $134_2$ can be activated to impart rotation of a screw $150_2$ rotatably connected about second axis $132_2$ to fourth body portion $142$. Fourth body portion $142$ is bevel shaped and may include a nut $152_2$ which is fitted into bevel shaped slot on third body portion $140$. Screw $150_2$ is connected to nut $152_2$. This arrangement, when second actuator $134_2$ drives screw $150_2$ to rotate, allows fourth body portion $142$ to slide smoothly on third body portion $140$ as the bevel shape restricts rotary motion of fourth body portion $142$. In this way, rotary motion of screw $150_2$ drivingly connected to fourth body portion $142$ converts rotary to linear motion resulting in fourth body portion $142$ to move between a retracted and an extended position.

Figure 3A:
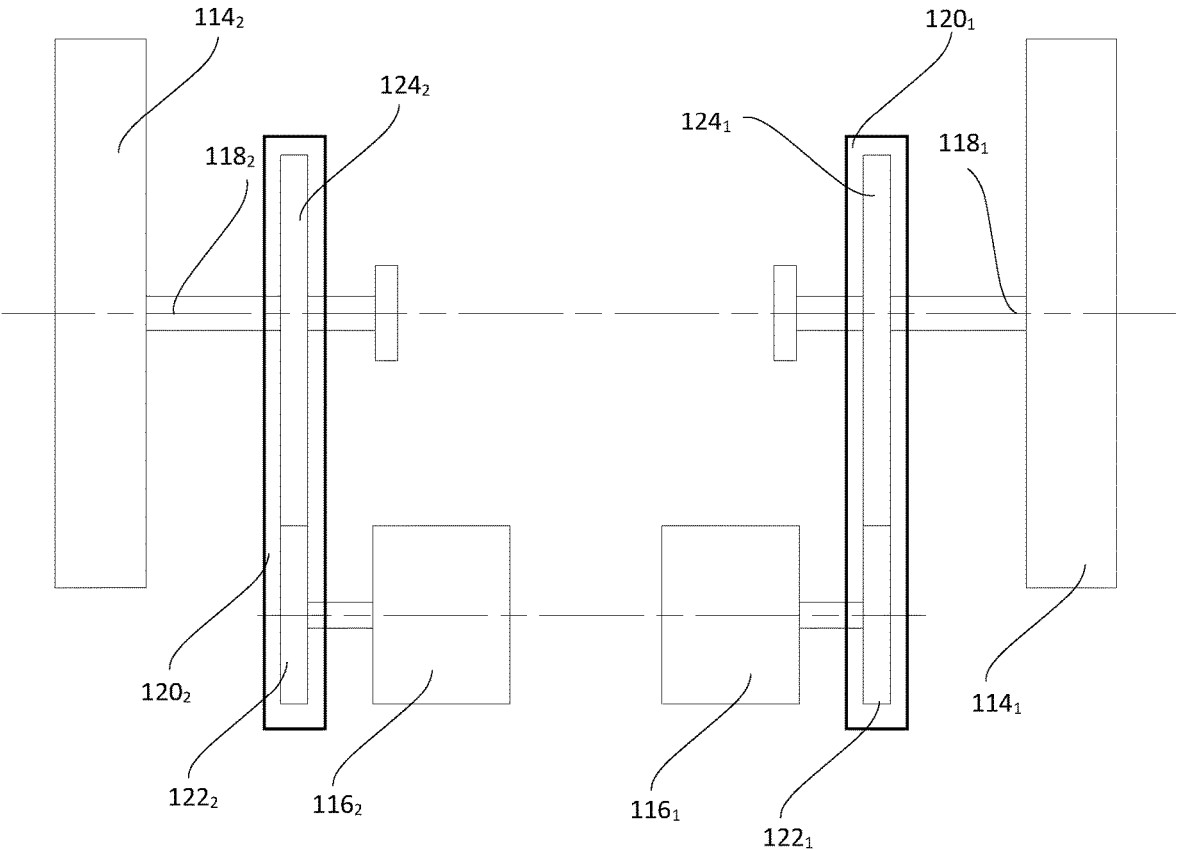
FIG. 3A is a side view of the unmanned vehicle with a section along line 2-2 in FIG. 3.

Referring to FIGS. 3-3A, unmanned vehicle $110$ may include one or more actuators $116$ that, when activated, collectively act to move unmanned vehicle $110$ relative to a fixed point in space. For example, the actuator(s) $116$ may form part of unmanned vehicle $110$ as shown in FIG. 3. Unmanned vehicle $110$ also includes controller $210$ that is communicatively coupled to actuator(s) $116$ to send control signals that activate actuator(s) $116$ to perform a movement automatically. Both articulated body $130$ as well as unmanned vehicle $110$ may also be operable by a teach pendent $212$ connected by a cable $204$. Actuator(s) $116$ may act to impart any movement upon unmanned vehicle $110$. For example, each actuator $116$ may act to rotate unmanned vehicle $110$, translate unmanned vehicle $110$, or move unmanned vehicle $110$ in more complex patterns involving both rotation and translation in one or more directions. In some embodiments, actuator(s) may be operable to rotate unmanned vehicle about third axis $108_3$ and translate unmanned vehicle $110$ along first and second axes $108_1$ and $108_2$ respectively. This may be achieved by any number of actuators $116$.

Still referring to FIG. 3-3A, unmanned vehicle $110$ may include a first actuator $116_1$ that acts to rotate a first wheel $114_1$ about first wheel axis $118_1$ and a second actuator $116_2$ that acts to rotate a second wheel $114_2$ about second wheel axis $118_2$. First and second wheel axes $118_1$ and $118_2$ are parallel with an offset between them as minimal as possible. As shown, actuator(s) $116$ can be any device that acts to impart movement upon wheel(s) $114$ in response to control signals (e.g. electrical signals) from controller $210$. For example, actuator(s) $116$ may include servos, DC or AC motors, fluid piston cylinders, or another type of actuator. In the illustrated example, unmanned vehicle $110$ may include a first gearbox $120_1$ that transmits motion from first actuator $116_1$ to first wheel $114_1$ and a second gearbox $120_2$ that transmits motion from second actuator $116_2$ to second wheel $114_2$. Gearbox(es) $120$ can be any mechanism that reduces the velocity it received from actuator(s) $116$ and the reduced velocity is then transmitted to wheel(s) $114$. As shown, gearbox(es) $120$ may include a pinion(s) $122$ and a gear(s) $124$. For example, first gearbox $120_1$ includes a first pinion $122_1$ meshed with a first gear $124_1$ that finally, connected to first wheel $114_1$. Hence, the velocity of first pinion $122_1$, when transmitted to first gear $124_1$, is reduced by a factor which is the ratio of the diameters of first gear $124_1$ and first pinion $122_1$. First gearbox $120_1$ also increases the torque by the same factor as well. Second gearbox $120_2$ includes a second pinion $122_2$ meshed with a second gear $124_2$ that finally, connected to second wheel $114_2$. Hence, the velocity of second pinion $122_2$, when transmitted to second gear $124_2$, is reduced by a factor which is the ratio of the diameters of second gear $124_2$ and second pinion $122_2$. Second gearbox $120_2$ also increases the torque by the same factor as well.

Still referring to FIG. 3, controller $210$ controls the velocity of actuator(s) $116$. When the speed of first and second actuator(s) $116_1$ and $116_2$ are equal unmanned vehicle $110$ moves linearly along a straight-line path which is parallel to axis $108_2$. However, when the speed of first and second actuator(s) $116_1$ and $116_2$ are not equal unmanned vehicle $110$ moves along a curvilinear path. And, when the speed of first and second actuator(s) $116_1$ and $116_2$ are equal in magnitude but opposite in direction unmanned vehicle $110$ rotates about its vertical axis $108_3$. Unmanned vehicle $110$ does not have any steering wheel. Instead, difference of wheel velocity is used to mimic the function of a steering wheel.

Figure 4:
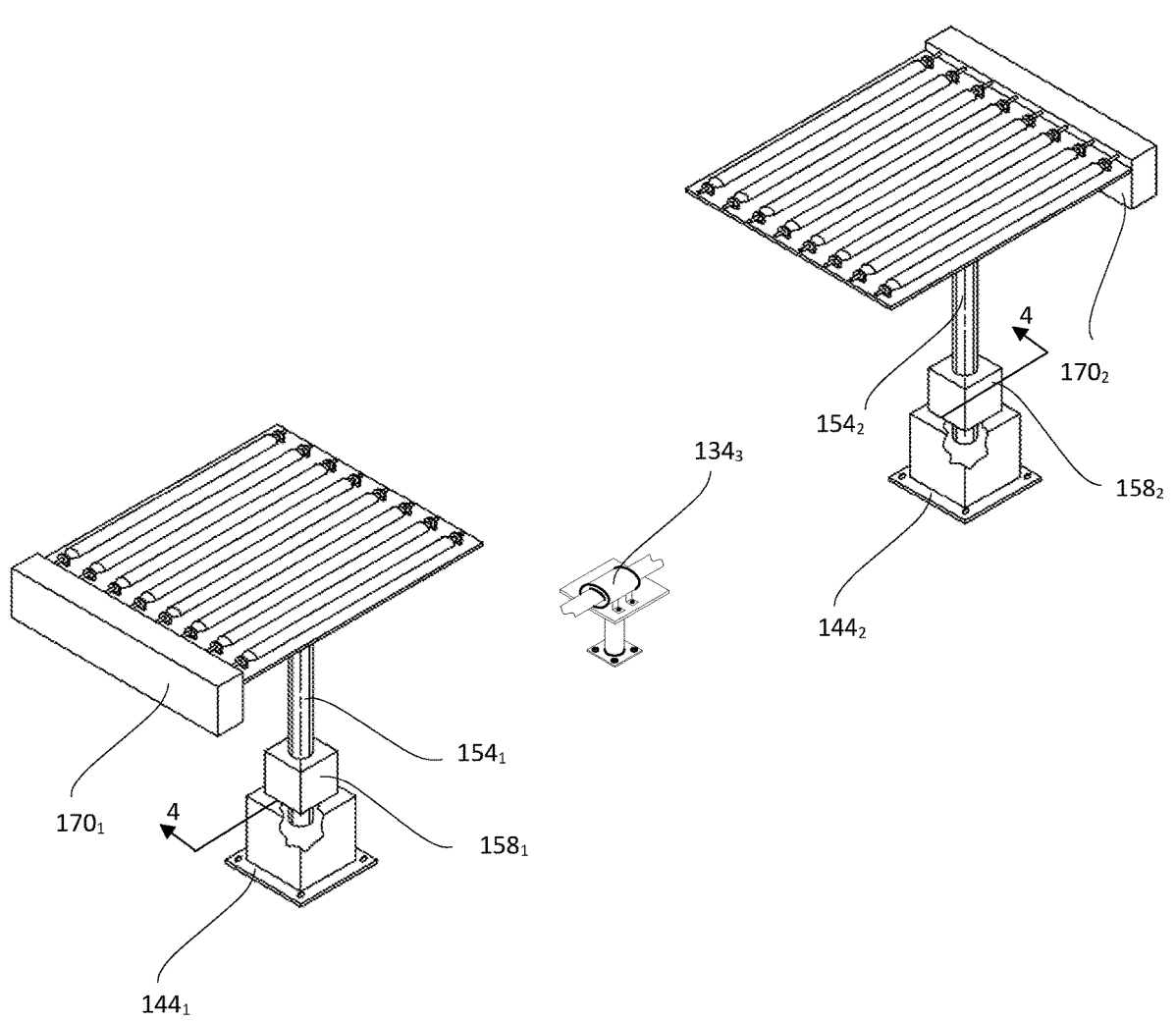
FIG. 4 is a perspective view of the third body portion of the articulated body.
Figure 5:
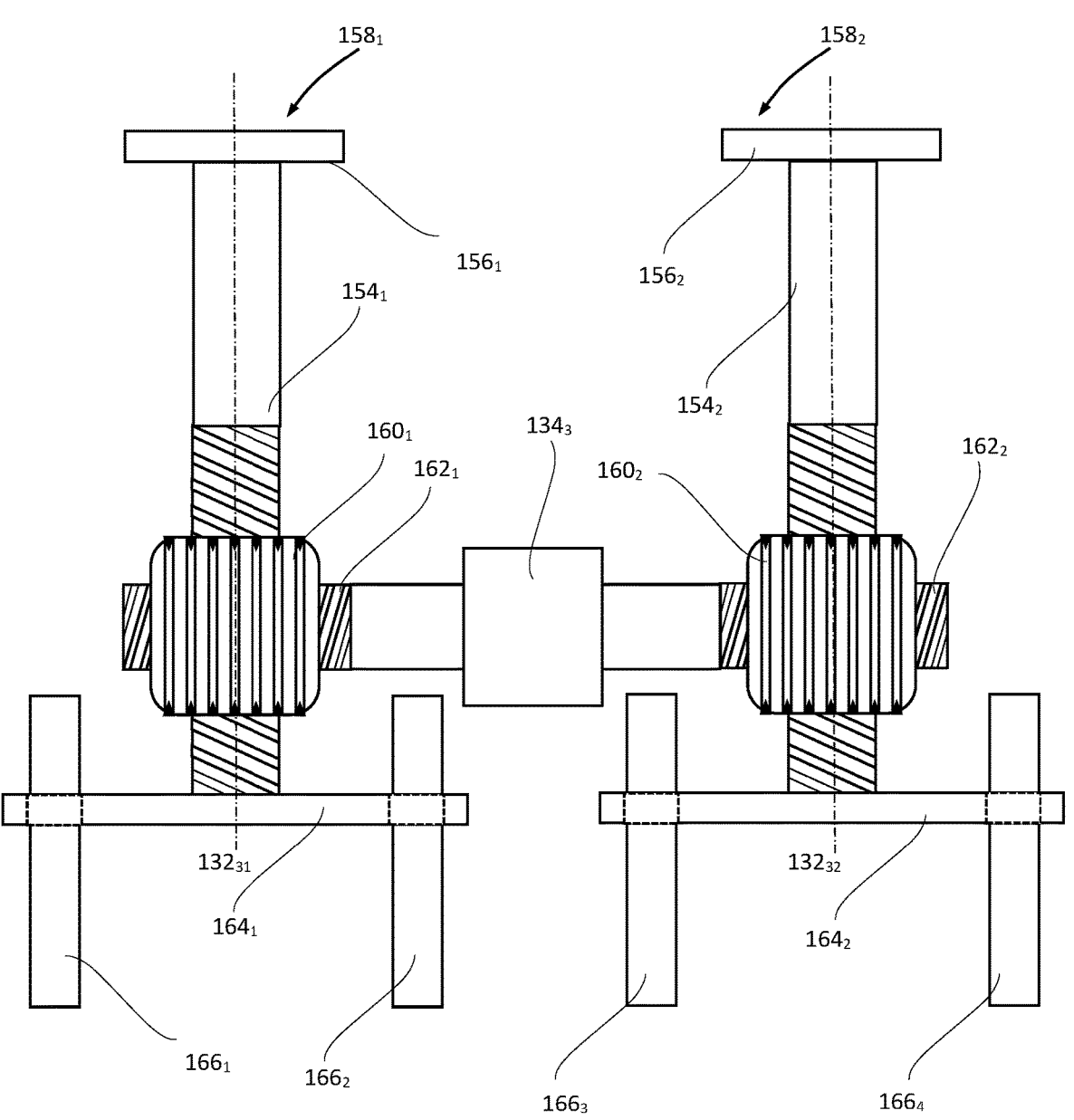
FIG. 5 is a side view of the third body portion with a section along line 4-4 in FIG. 4.

Referring to FIGS. 4-5, fifth body portion(s) $144$ is shown in accordance with an embodiment. As shown, fifth body portion(s) $144$ includes a screw shaft(s) $154$ and an actuator $134_3$. Screw shaft(s) $154$ has a distal end $156$ to which rolling bed $170$ is mounted in use. Screw shaft(s) $154$ is movable between an extended position and a retracted position by the operation of actuator $134_3$. Actuator $134_3$ may be a rotary-type actuator, such as a servo, and drivingly connected to screw shaft(s) $154$ indirectly by a mechanism that converts rotary to linear movement. For example, screw jack(s) $158$ as illustrated in FIG. 5 is one such mechanism. Screw jack(s) $158$ may include any gear arrangement that may convert rotary movement of rotary actuator $134_3$ into linear movement of screw shaft(s) $154$ moving screw shaft(s) $154$ between a retracted position and an extended position. In case of twin screw jacks $158$, actuator $134_3$ may be a dual shaft actuator and may be directly connected to a first screw jack $158_1$ on the left-hand side and a second screw jack $158_2$ on the right-hand side. In case of single shaft actuator for twin screw jacks $158$, rotary motion needs to be transferred from single shaft actuator to first screw jack $158_1$ as well as second screw jack $158_2$. First screw jack $158_1$ and second screw jack $158_2$ are identical in design. First screw jack $158_1$ may include a first worm $162_1$ that is drivingly connected to actuator $134_3$. First worm $162_1$ may be any worm that can transmit power to a first worm gear $160_1$, when in mesh. First worm gear $160_1$ is any worm gear that has gear teeth on the outer periphery and thread on the inner periphery. Because of both gear and thread, first worm gear $162_1$ acts like a gear as well as a nut. While the outer teeth of first worm gear $160_1$ meshes with the helical thread on first worm $162_1$ the inner thread of first worm gear $160_1$ connects first worm gear $160_1$ to first screw shaft $154_1$ resulting in a linear vertical motion of first screw shaft $154_1$ along vertical axis $132_{31}$. Second screw jack $158_2$ may include a second worm $162_2$ that is drivingly connected to actuator $134_3$. Second worm $162_2$ may be any worm that can transmit power to a second worm gear $160_2$, when in mesh. Second worm gear $160_2$ is any worm gear that has both gear teeth on the outer periphery and thread on the inner periphery. Because of both gear and thread, second worm gear $162_2$ acts like a gear as well as a nut. While the outer teeth of second worm gear $160_2$ meshes with the helical thread on second worm $162_2$ the internal thread of second worm gear $160_2$ connects second worm gear $160_2$ to first screw shaft $154_2$ resulting in a linear vertical motion of second screw shaft $154_2$ along vertical axis $132_{32}$.

Figure 6A:
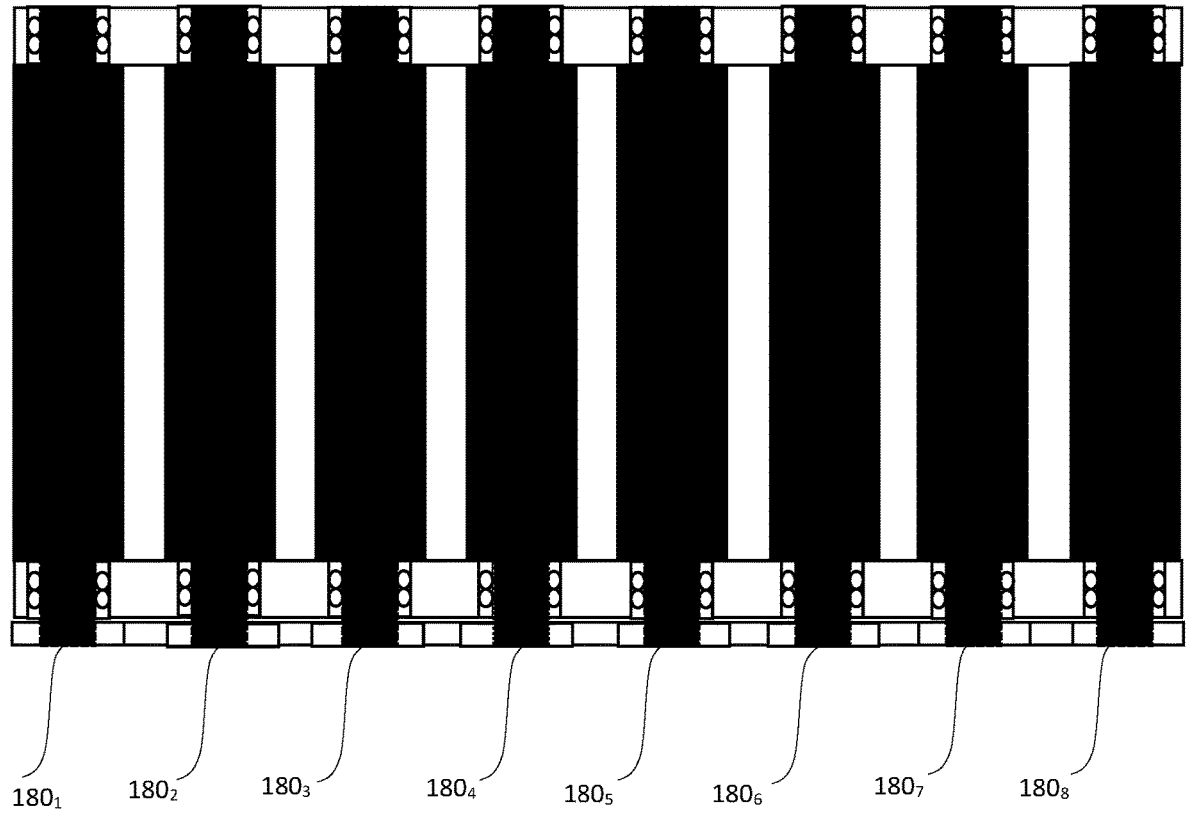
FIG. 6A is a top view of the rolling bed.
Figure 6B:
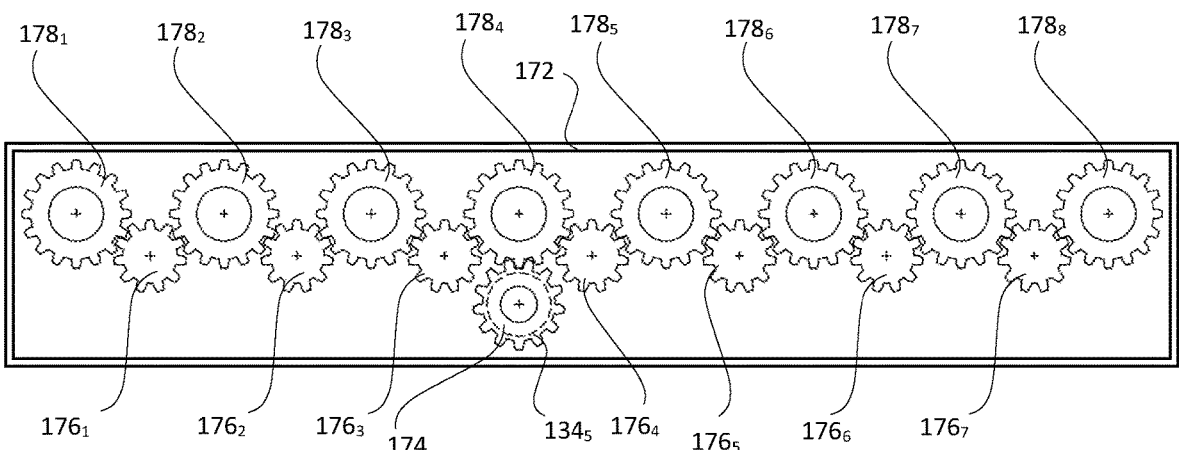
FIG. 6B is a front view of the rolling bed.
Figure 6C:
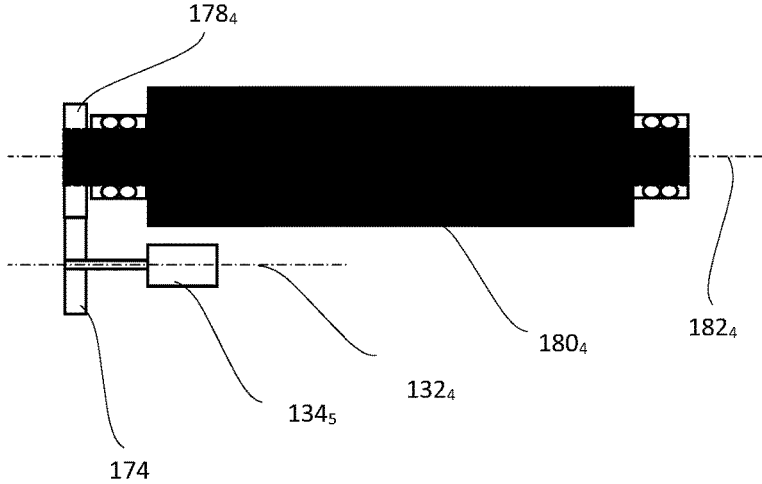
FIG. 6C is a side view of the rolling bed.

Referring to FIGS. 6A, 6B and 6C, rolling bed 170 is shown in three different views—top, front and side respectively. Rolling bed 170 includes a plurality of cylindrical roller(s) 180 and an actuator $134_5$. Actuator $134_5$ may be a rotary-type actuator, such as a servo, and drivingly connected to roller(s) 180 indirectly by a gearbox 172 that transmits the rotary motion of actuator $134_5$ to the rotary motion of roller(s) 180. For example, actuator $134_5$ may be directly connected to a pinion 174 which is any pinion that can transmit rotary motion between two parallel axes lying on a same plane. Actuator $134_5$ rotates about an axis $132_4$. Pinion 174 rotates about an axis which is same as the axis of rotation of actuator $134_5$, i.e., axis $132_4$. Similarly, each roller rotates with a same uniform velocity in the same direction about an axis called roller axis(es) 182. As shown, there are eight rollers and so are eight roller axes 182. Therefore, axis $132_4$ may be parallel to any of roller axes 182 and may lie on a same plane. As illustrated in FIG. 6C, axis $132_4$ is parallel to fourth roller axis $182_4$ and lies on the same vertical plane.

Referring to FIGS. 6B and 6C, Gearbox 172 includes one or more gears 178 of same diameter that transfer rotary motion from pinion 174 to rollers 180. For example, fourth gear $178_4$ may be connected to fourth roller $180_4$ and rotate about fourth roller axis $182_4$. Fourth gear $178_4$ may be any gear that is connected to pinion 174 thereby transfers rotary motion from pinion 174 to fourth roller $180_4$. Gear box 172 may include idle gear(s) 176 to transmit rotary motion from fourth gear $178_4$ to all other gears 178 which are, in turn, connected to all other rollers 180 thereby transmits rotation from fourth gear $180_4$ to all other rollers 180. Idle gears 176 also helps maintaining the same direction of rotation of all rollers 180. For example, fourth gear $178_4$ transmits rotation to both third idle gear $176_3$ and fourth idle gear $176_4$ thereby changes direction of rotation of fourth gear $178_4$. However, third idle gear $176_3$ and fourth idle gear $176_4$, when transmit rotation to third gear $178_3$ and fifth gear $178_5$ respectively, change the direction again thereby bring the direction back to the same direction as the direction of rotation of fourth gear $178_4$ was. As third roller $180_3$ and fifth roller $180_5$ are connected to third gear $178_3$ and fifth gear $178_5$ respectively, third roller $180_3$ and fifth roller $180_5$ rotate with same velocity and in same direction.

Third gear $178_3$ drives second idle gear $176_2$ thereby changes direction of rotation of third gear $178_3$. However, second idle gear $176_2$, when transmits rotation to second gear $178_2$, changes the direction again thereby bring the direction back to the same direction as the direction of rotation of third gear $178_3$ was. As second gear $178_2$ is rigidly connected to second roller $180_2$, both second gear $178_2$ and second roller $180_2$ rotate in unition. Second gear $178_2$ drives first idle gear $176_1$ thereby changes direction of rotation of second gear $178_2$. However, first idle gear $176_1$, when transmits rotation to first gear $178_1$, changes the direction again thereby bring the direction back to the same direction as the direction of rotation of second gear $178_2$ was. As first gear $178_1$ is rigidly connected to first roller $180_1$, both first gear $178_1$ and first roller $180_1$ rotate in unition.

Fifth gear $178_5$ drives fifth idle gear $176_5$ thereby changes direction of rotation of fifth gear $178_5$. However, fifth idle gear $176_5$, when transmits rotation to sixth gear $178_6$, changes the direction again thereby bring the direction back to the same direction as the direction of rotation of fifth gear $178_5$ was. As sixth gear $178_6$ is rigidly connected to sixth roller $180_6$, both sixth gear $178_6$ and sixth roller $180_6$ rotate in unition. Sixth gear $178_6$ drives sixth idle gear $176_6$ thereby changes direction of rotation of sixth gear $178_6$. However, sixth idle gear $176_6$, when transmits rotation to seventh gear $178_7$, changes the direction again thereby bring the direction back to the same direction as the direction of rotation of sixth gear $178_6$ was. As seventh gear $178_7$ is rigidly connected to seventh roller $180_7$, both seventh gear $178_7$ and seventh roller $180_7$ rotate in unition. Seventh gear $178_7$ drives seventh idle gear $176_7$ thereby changes direction of rotation of second gear $178_7$. However, seventh idle gear $176_7$, when transmits rotation to eight gear $178_8$, changes the direction again thereby bring the direction back to the same direction as the direction of rotation of seventh gear $178_7$ was. As eighth gear $178_8$ is rigidly connected to eighth roller $180_8$, both eighth gear $178_8$ and eighth roller $180_8$ rotate in unition.

Figure 7:
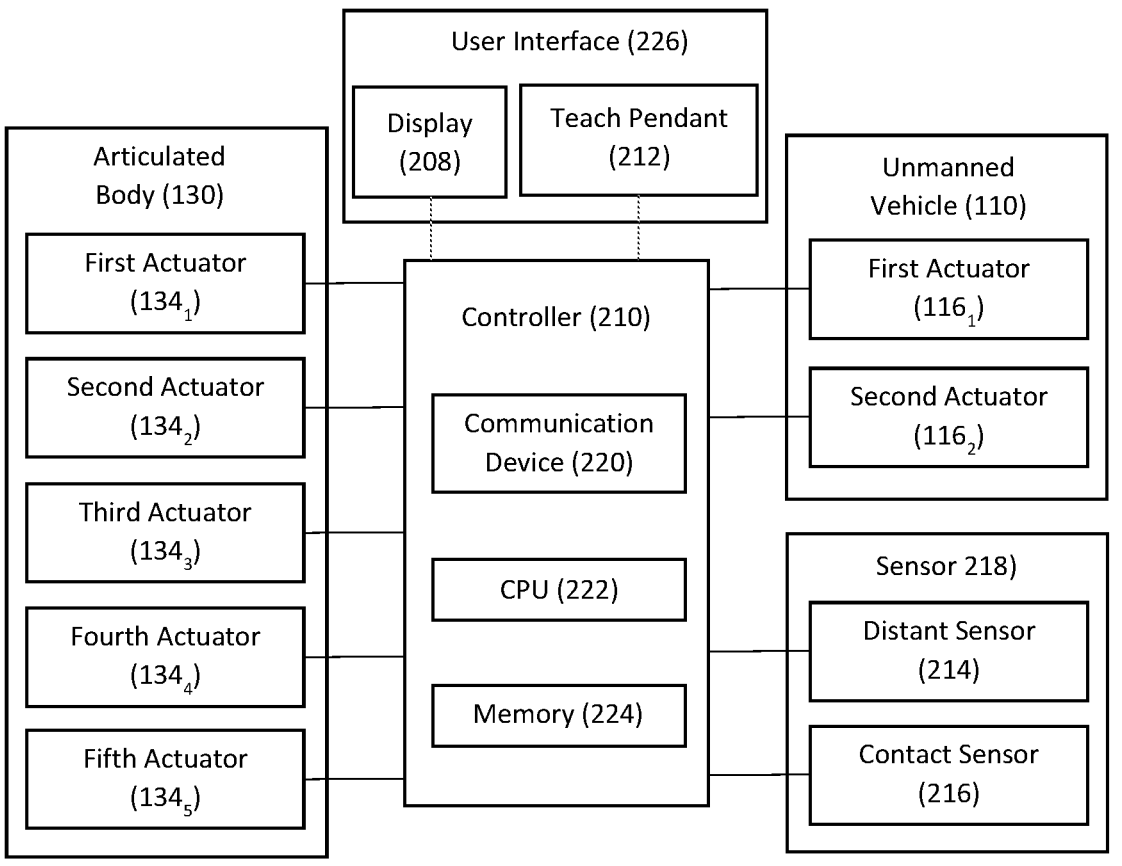
FIG. 7 is a schematic illustration of a controller communicatively coupled to various components.

Reference is now made to FIG. 7, which shows a schematic illustration of controller 210 in accordance with an embodiment. As shown, controller 210 may include a processor (hardware) 222 and memory 224 that are communicatively coupled to actuators 134 of articulated body 130, actuators 116 of unmanned vehicle 110, sensor(s) 218 and user-interface member(s) 226. Processor 222 may be any device that can send control signals, wirelessly or by wire, that activate actuators 136 and actuators 116 if present, in accordance with instructions (e.g. a payload lift or transfer program) stored in memory 224.

In some embodiments, execution of instructions from memory 224 relies in part on user inputs from user-interface member(s) 226 and/or information from sensor(s) 218. As seen in FIG. 3, user-interface member(s) 226 may include a teach pendant 212 or a display 208 (e.g. electronic display), user input controls (e.g. buttons), a speaker, and a microphone for example. Returning to FIG. 7, controller 210 includes a communication device 220 that allows for one or both of wired communication (e.g. by USB) or wirelessly communication (e.g. by 802.11x, Bluetooth, or infrared). In some embodiments, a user may send instructions to controller 210 from an external device (e.g. computer or smartphone) by wire or wireless through communications device 220. Controller 210 may be positioned anywhere on robotic transfer device 100. For example, controller 210 may be positioned within articulated body 130. In the illustrated example, controller 210 is positioned within unmanned vehicle 110 as shown in FIG. 3 and enclosed with mount 112. In order to avoid repetitive reference to FIG. 7, the reader is directed to refer to FIG. 7 in connection with any mention hereafter of controller 210 or components thereof.

Referring to FIG. 7 and FIG. 3, in some embodiments, robotic transfer device 100 includes distance sensors 214 and contact sensors 216. Both distance sensors 214 and contact sensors 216 are communicatively coupled to processor 220. Distance sensors 214 can include any one or more devices that can collectively provide sensory information to controller 210 from which controller 210 can infer (e.g. determine) distance between any obstacle and distance sensors 214. For example, distance sensors 214 may include one or more of a lidar, sonar or infrared sensor. Distance sensors 214 may be located on unmanned vehicle and/or articulated body 130. As shown, unmanned vehicle 110 includes six distance sensors 214 at the front. While on the left front there are first distance sensor $214_1$, second distance sensor $214_2$ and third distance sensor $214_3$, on the right front there are forth distance sensor $214_4$, fifth distance sensor $214_5$ and sixth distance sensor $214_6$. Controller 210 may compute the path of unmanned vehicle 110 based on distance sensors 214 readings and then, drives actuator(s) 116 along the computed path to move unmanned vehicle 110. Controller 210 may avoid obstacles using first distance sensor $214_1$, second distance sensor $214_2$, fourth distance sensor $214_4$ and fifth distance sensor $214_5$. Controller 210 may also compute the path of articulated body 130 and then, drives actuator 134 along the computed path to move articulated body 130. For example, controller 210 may activate $134_3$ to move rolling bed 170 vertically upward based on the output of third distance sensor $214_3$ and sixth distance sensor $214_6$. Controller 210 may calculate the distance of payload 200 from rolling bed 170 by computing the mean of the values of third distance sensor $214_3$ and sixth distance sensor $214_6$. When the mean becomes equal to or less than a predetermined value, controller 200 understands that rolling bed 170 is in contact with payload 200. The predetermined value may be selected based on the characteristics of distance sensors $214_3$ and $214_6$ and the bottom surface of payload 200. At this point, controller 210 knows that rolling bed 170 is going to lift payload 200 and may need large force depending on the weight of payload 200. Controller 210 also knows at what height rolling bed 170 needs to be lifted.

In some embodiments, robotic transfer device 100 includes contact sensors 216 that are communicatively coupled to processor 220. Contact sensors 216 can include any one or more devices that can collectively provide sensory information to controller 210 from which controller 210 can infer (e.g. determine) contact between payload 200 and rolling bed 170 or any obstacle and unmanned vehicle 110. For example, contact sensor 216 may include one or more of a bumper, infrared sensor, accelerometer, or force sensor. Controller 210 may establish and/or maintain contact between rolling bed 170 and payload 200 based on reading from contact sensor. For example, controller 210 may activate $134_3$ to move rolling bed 170 vertically upward until controller 210 determines from contact sensor 216 that rolling bed 170 exerts a force on the bottom surface of payload 200 that is more than a predetermined force value. The predetermined force value may be selected based on the characteristics of contact sensor 216 and bottom surface of payload 210. At this point, controller 210 knows that rolling bed 170 is going to lift payload 200 and may need large force depending on the weight of payload 200. Controller 210 also knows at what height rolling bed 170 needs to be lifted.

In alternative embodiments, robotic transfer device 100 may not include a contact sensor 216. For example, robotic transfer device 100 may be integrated into or purpose build to lift a specific payload 200, whereby controller 210 is preconfigured with lift height. In some embodiments, robotic transfer device 100 may be user-configurable with input instruction for control parameter data as for example, parameter data file may be uploaded wirelessly.

Figure 8:
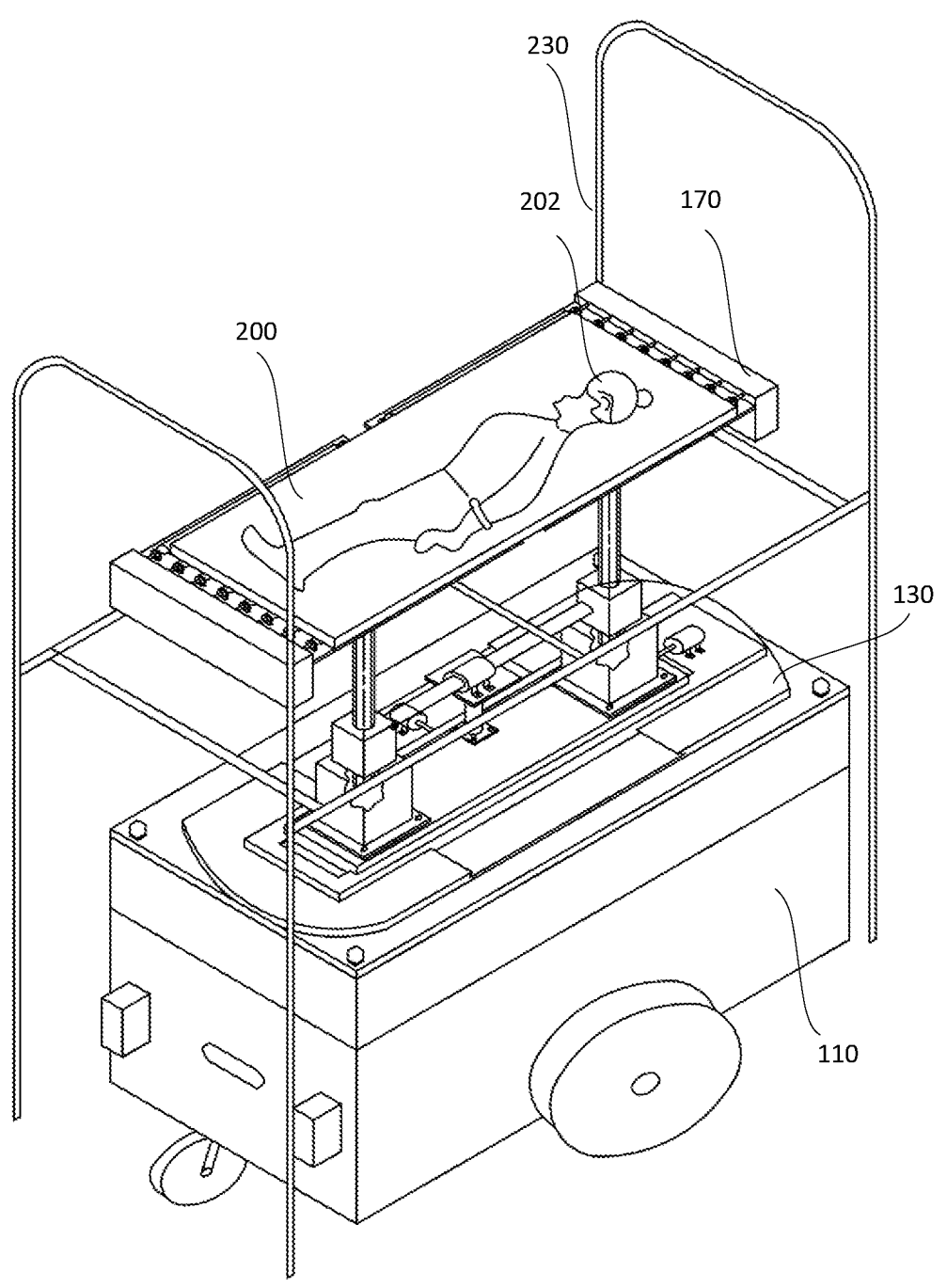
FIG. 8 is a perspective view of the robotic transfer device lifting a payload.

Now, referring to FIG. 8, in some embodiments, robotic transfer device 100 holds a payload 200 lifting the same from a bed frame 230. Robotic transfer device 100 may be operated by a teach pendent 212 wirelessly or connected by cable 204. Teach pendent 212 may include a display 208 and push buttons 206 or other devices such as knobs and joysticks as shown in FIG. 3. Display 208 may show various control parameters data using software interface with controller 210. Push buttons 206 may be used to operate unmanned vehicle 110 and articulated body 130. For example, unmanned vehicle 100 may be operable along a straight line, forward or backward by activating both first actuator $116_1$ and second actuator $116_2$ with same velocities. Unmanned vehicle 100 may be operable turning right or left-forward or backward by activating both first actuator $116_1$ and second actuator $116_2$ with different velocities. Push buttons 206 are used to operate articulated body 130 too. Articulated body 130 may be operable along axes $132_1$, $132_2$ and $132_3$ by activating first actuator $134_1$, second $134_2$ and third actuator $134_3$ respectively. Articulated body 130 may be operable to rotate about axis $134_3$ by activating fourth actuator $134_4$. When operated manually, the operator uses push buttons 206 to maneuver unmanned vehicle 110, sees the surrounding environment, avoids obstacles and brings unmanned vehicle 110 right under bed frame 230. Then, the operator maneuvers articulated body using push buttons 206 to position rolling bed 170 right under payload 200. Payload 200 may include a patient 202. The operator activates third actuator $134_3$ upward to lift payload 200.

Alternatively, robotic transfer device 100 may be operable autonomously. In this case, the destination of unmanned vehicle 110 is to be fed into controller 210 by the operator. Controller 210 computes the path and the speed of actuators 116 with respect to time for unmanned vehicle 110 so that unmanned vehicle 110 is able to reach to the said destination. Then, controller 210 activates both first actuator $116_1$ and second actuator $116_2$ simultaneously, avoids obstacles using sensors 216 and if needed, re-calculates the path and the speed of actuators 116 with respect to time for unmanned vehicle 110 to reach to the said destination. After reaching, controller 210 computes the path of articulated body 130 to make contact with payload 200. Controller 210 also calculates the speed of first actuator $134_1$, second actuator $134_2$, third actuator $134_3$ and fourth actuator $134_4$ and activates actuators 134 to have contact between rolling bed 170 and payload 200. In some embodiment, rolling bed 170 may include contact sensor 216 that sends signal to controller 210 when a contact is made by rolling bed 170 with payload 210. Finally, controller 210 activates actuator $134_4$ to lift payload 200 to a certain height. This height may vary application to application and is a parameter to be set by the user.

Figure 9:
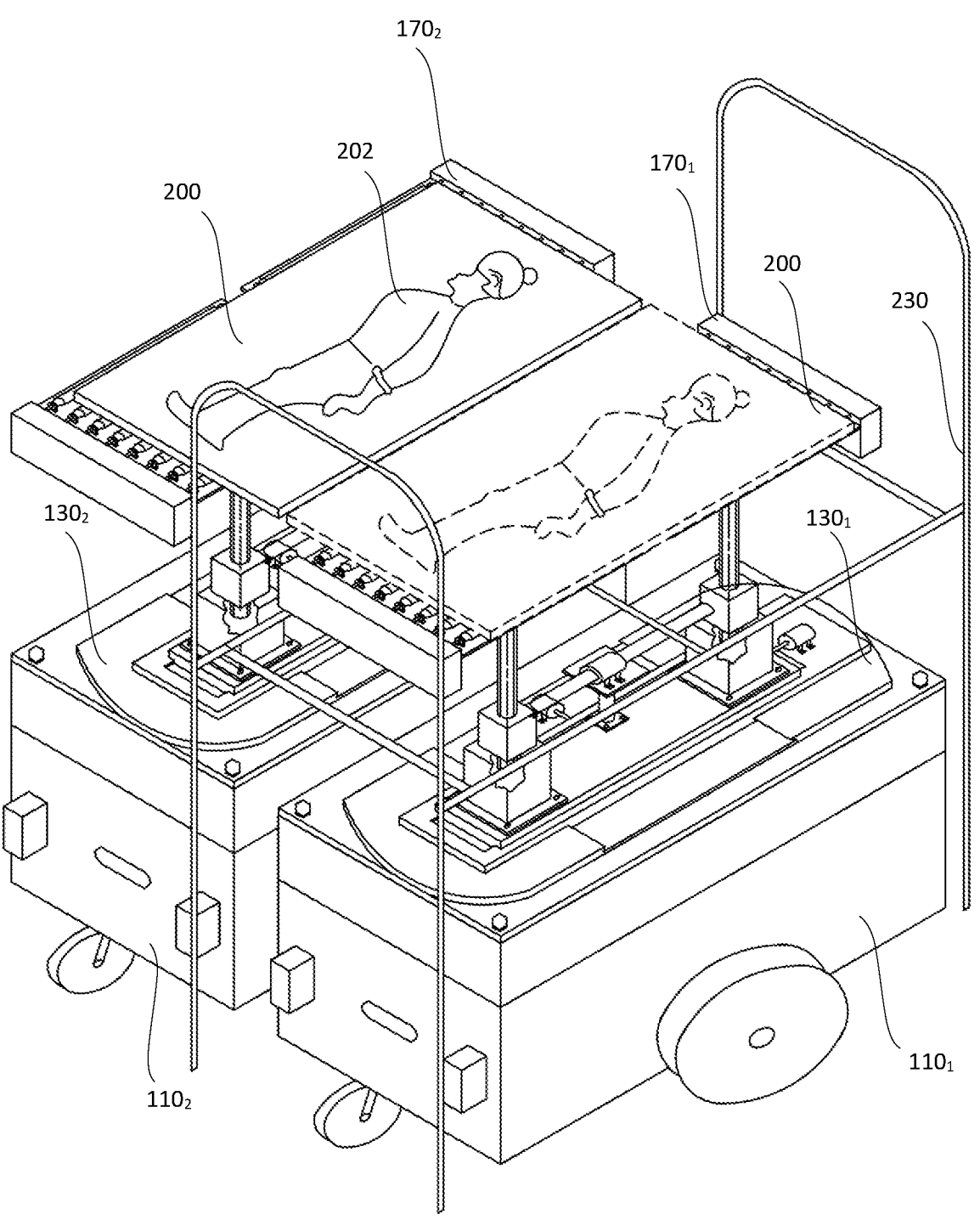
FIG. 9 is a perspective view of two robotic transfer devices cooperating with each other transferring a payload from one robotic transfer device to other.

FIG. 9 shows two robotic transfer devices 100. For example, first robotic transfer device $100_1$ is on the right-hand side holding a payload 200 and second robotic transfer device $100_2$ is on the left-hand side ready to receive payload 200 from first robotic transfer device $100_1$. The two positions of robotic transfer devices 100 may be any but stationed side-by-side such that payload 200 including patient 202 may be transferred by first robotic transfer device $100_1$ to second robotic transfer device $100_2$. As explained above, second robotic device $100_2$ may be operated either manually or autonomously. When operated manually, teach pendent 212 is used. The operator uses push buttons 206 to maneuver unmanned vehicle 110 of second robotic transfer device $100_2$, looks around the surrounding environment, avoids obstacles and brings unmanned vehicle 110 right beside first robotic transfer device 100₁. Then, the operator maneuvers articulated body using push buttons 206 to position rolling bed 170 right beside rolling bed 170 of first robotic transfer device 100₁ as shown in FIG. 9. Payload 200 may include a patient 202. The height of rolling bed 170 of second robotic transfer device 100₂ is maintained same as the height of rolling bed 170 of first robotic transfer device 100₁. Both rolling beds 170 of two robotic transfer devices 100 are aligned parallel. The gap between two rolling beds 170 is very small and is such that payload 200 would not slip through the gap and fall down when transfer operation from first robotic transfer device 100₁ to second robotic transfer device 100₂ would be performed. When the operator using teach pendant 212 activates fifth actuators 134₅ of both robotic transfer devices 100, all rollers 180 of both rolling beds 170 start rotating in a same direction with a same angular velocity thereby move payload 200 including patient 202 along one direction perpendicular to the axis of rotation of rollers 180. The direction of the angular velocity is such that payload 200 moves along a direction which leads to move payload 200 from first robotic transfer device 100₁ to second robotic transfer device 100₂. The operator observes the motion and stops fifth actuators 134₅ of both robotic transfer devices 100 when the transfer operation of payload 200 is finished.

The transfer operation may be carried out autonomously too without using the teach pendant 212. In this case, the destination of second robotic transfer device 100₂ is to be fed into controller 210 by an operator. Controller 210 computes the path and the speed of actuators 116 with respect to time for unmanned vehicle 110 of second robotic device 100₂ so that unmanned vehicle 110 can reach the said destination. Then, controller 210 activates both first actuator 116₁ and second actuator 116₂ of second robotic transfer device 100₂ simultaneously, avoids obstacles using sensors 218 and if may re-calculate the path and the speed of actuators 116 with respect to time for unmanned vehicle 110 to reach the said destination. After reaching, controller 210 computes the path of articulated body 130 to position rolling bed 170 right beside rolling bed 170 of first robotic transfer device 100₁ as shown in FIG. 9. The height of rolling bed 170 of second robotic transfer device 100₂ is maintained same as the height of rolling bed 170 of first robotic transfer device 100₁. Now, controller 210 calculates the speed of first actuator 134₁, second actuator 134₂, third actuator 134₃ and fourth actuator 134₄ and activates actuators 134 to move rolling bed 170 od second robotic transfer device 100₂ to desired location. Both rolling beds 170 of two robotic transfer devices 100 are now aligned parallel. The gap between two rolling beds 170 is very small and is such that payload 200 would not slip through the gap and fall down when transfer operation from first robotic transfer device 100₁ to second robotic transfer device 100₂ would be performed. Finally, controller 210 activates fifth actuators 134₅ of both robotic transfer devices 100 and as a result, all rollers 180 of both rolling beds 170 start rotating in the same direction with a same angular velocity thereby move payload 200 including patient 202 along one direction perpendicular to the axis of rotation of rollers 180. The direction of the angular velocity is such that payload 200 moves along a direction which leads to move payload from first robotic transfer device 100₁ to second robotic transfer device 100₂. Controller 210 monitors the movement and stops fifth actuators 134₅ of both robotic transfer devices 100 when the transfer operation of payload 200 is finished.

The invention claimed is:

1. A robotic transfer device for transferring a payload, the robotic transfer device comprising:
   at least one rolling bed; and
   an articulated body coupled to the rolling bed, the articulated body having a fixed base and one or more actuators that collectively move the rolling bed from a first pose to another pose wherein each pose includes both position and orientation in three-dimensional space,
      the one or more actuators, when activated manually or autonomously, collectively translate the rolling bed relative to the fixed base along first, second and third axes and rotate the rolling bed about the third axis relative to the fixed base,
      the one or more actuators include a first actuator that translates the rolling bed along the first axis independently, a second actuator that translates the rolling bed along the second axis independently, a third actuator that translates the rolling bed along the third axis, also known as yaw axis, independently, and a fourth actuator that rotates the rolling bed about the same third axis independently, all the said translations and rotation are relative to the fixed base.

2. The robotic transfer device of claim 1, further comprising:
   a controller communicatively coupled to the one or more actuators to send control signals that direct the one or more actuators to translate and rotate the rolling bed.

3. The robotic transfer device of claim 2, further comprising:
   one or more distance sensors communicatively coupled to the controller to send sensor readings to the controller indicative of distance between an obstacle and/or a payload and the articulated body.

4. The robotic transfer device of claim 2, further comprising:
   one or more contact sensors communicatively coupled to the controller to send sensor readings to the controller indicative of contact between an obstacle and/or payload and the robotic transfer device.

5. The robotic transfer device of claim 2, wherein:
   in response to a user instruction, the controller sends control signals to the one or more actuators to execute a moving operation in which the rolling bed is moved into contact with a surface of the payload.

6. The robotic transfer device of claim 1, further comprising:
   at least one extension shaft having a distal end, wherein the rolling bed is mounted to the distal end of the extension shaft, and one or more extension shaft actuators act to move the extension shaft between an extended pose and a retracted pose wherein each pose includes both position and orientation in the three-dimensional space.

7. The robotic transfer device of claim 1, wherein:
   the rolling bed includes a plurality of cylindrical rollers forming a bed.

8. The robotic transfer device of claim 7, wherein:
   the rolling bed includes an actuator that drives the cylindrical rollers resulting in each cylindrical roller to rotate about an axis of rotation of the cylindrical roller.

9. An autonomous robotic transfer device for transferring a payload by an unmanned vehicle, the autonomous robotic transfer device comprising:
   an unmanned vehicle having one or more actuators that collectively move the unmanned vehicle autonomously relative to a fixed point in a three-dimensional space;

at least one rolling bed;

an articulated body coupled to the rolling bed and mountable to the unmanned vehicle, the articulated body having one or more actuators that collectively move the rolling bed relative to the unmanned vehicle, the one or more actuators, when activated manually or autonomously, collectively translate the rolling bed relative to the unmanned vehicle along first, second and third axes and rotate the rolling bed about the third axis relative to the unmanned vehicle, the one or more actuators of the unmanned vehicle includes a first actuator that translates the unmanned vehicle along a longitudinal axis, also known as roll axis, and a second actuator that translates the unmanned vehicle along the same longitudinal axis or roll axis as the first actuator; and a controller communicatively coupled to the one or more actuators to send control signals that direct the one or more actuators to translate and rotate the rolling bed.

10. The autonomous robotic transfer device of claim 9, wherein:

a combination of equal and same directional velocities of the first and second actuator translates the unmanned vehicle along the longitudinal axis or roll axis, a combination of unequal and same directional velocities of the first and second actuator translates the unmanned vehicle along the longitudinal axis or roll axis as well as a transverse axis, also known as pitch axis, the transverse axis or the pitch axis being perpendicular to the longitudinal axis or roll axis on a plane on which the unmanned vehicle is moving, and rotates the unmanned vehicle about a vertical axis, also known as yaw axis, the vertical or yaw axis being mutually perpendicular to both the longitudinal as well as transverse axes, and a combination of equal but mutually opposite directional velocities of the first and second actuator rotates the unmanned vehicle about the vertical axis or yaw axis.

11. The autonomous robotic transfer device of claim 9, wherein:

in response to a user instruction, the controller sends control signals to the one or more actuators to execute a moving operation in which either the unmanned vehicle is moved, or the rolling bed is moved, or both the unmanned vehicle and the rolling bed are moved, or rollers of the rolling bed rotate, or any combination of complex movement takes place.

12. The autonomous robotic transfer device of claim 9, further comprising:

a mount securable to the unmanned vehicle; and a connector coupled to the articulated body and removably connectable to the mount.

13. A method of robotically transferring a payload, the method comprises:

moving a first autonomous robotic transfer device under the payload wherein:

the first autonomous robotic transfer device comprising:

a first unmanned vehicle having a first set of one or more actuators that collectively move the first unmanned vehicle autonomously relative to a fixed point in a three-dimensional space;

at least one rolling bed;

an articulated body coupled to the rolling bed and mountable to the first unmanned vehicle, the articulated body having a second set of one or more actuators that collectively move the rolling bed relative to the first unmanned vehicle, the second set of one or more actuators, when activated manually or autonomously, collectively translates the rolling bed relative to the first unmanned vehicle along first, second and third axes and rotate the rolling bed about the third axis relative to the first unmanned vehicle, the second set of one or more actuators include a first actuator that translates the rolling bed along the first axis independently, a second actuator that translates the rolling bed along the second axis independently, a third actuator that translates the rolling bed along the third axis, also known as yaw axis, independently, and a fourth actuator that rotates the rolling bed about the same third axis independently all the said translations and rotation are relative to the fixed base; and a controller communicatively coupled to the first set of one or more actuators as well as the second set of one or more actuators to send control signals that direct the first set of one or more actuators as well as the second set of one or more actuators to translate and rotate the rolling bed;

lifting the payload by the first autonomous robotic transfer device;

moving a second autonomous robotic transfer device near the payload wherein:

the second autonomous robotic transfer device comprising:

a second unmanned vehicle having a first set of one or more actuators that collectively move the second unmanned vehicle autonomously relative to a fixed point in a three-dimensional space;

at least one rolling bed;

an articulated body coupled to the rolling bed and mountable to the second unmanned vehicle, the articulated body having a second set of one or more actuators that collectively move the rolling bed relative to the second unmanned vehicle, the second set of one or more actuators, when activated manually or autonomously, collectively translates the rolling bed relative to the second unmanned vehicle along first, second and third axes and rotate the rolling bed about the third axis relative to the second unmanned vehicle, the second set of one or more actuators include a first actuator that translates the rolling bed along the first axis independently, a second actuator that translates the rolling bed along the second axis independently, a third actuator that translates the rolling bed along the third axis, also known as yaw axis, independently, and a fourth actuator that rotates the rolling bed about the same third axis independently, all the said translations and rotation are relative to the fixed base; and a controller communicatively coupled to the first set of one or more actuators as well as the second set of one or more actuators to send control signals that direct the first set of one or more actuators as well as the second set of one or more actuators to translate and rotate the rolling bed; and transferring the payload from the first autonomous robotic transfer device to the second autonomous robotic transfer device.

14. The method of claim 13 wherein moving the first autonomous robotic transfer device under the payload comprises:

computing a path for the first unmanned vehicle of the first autonomous robotic transfer device;

driving the first unmanned vehicle of the first autonomous robotic transfer device along the said path; and positioning the rolling bed of the first autonomous robotic transfer device under the payload.

15. The method of claim 14, wherein positioning the rolling bed of the first autonomous robotic transfer device under the payload comprises:

computing a path for the rolling bed of the first autonomous robotic transfer device; and driving the rolling bed of the first autonomous robotic transfer device along the said path.

16. The method of claim 13, wherein lifting the payload by the first autonomous robotic transfer device comprises:

moving the rolling bed of the first autonomous robotic transfer device into contact with a plurality of locations of the payload; and driving the articulated body of the first autonomous robotic transfer device along an axis parallel to the third axis of the said articulated body of the first autonomous robotic transfer device.

17. The method of claim 13 wherein moving the second autonomous robotic transfer device near the payload comprises:

computing a path for the second unmanned vehicle of the second autonomous robotic transfer device;

driving the second unmanned vehicle of the second autonomous robotic transfer device along the said path; and positioning as well as aligning the rolling bed of the second autonomous robotic transfer device to a height equal to the height of the rolling bed of the first autonomous robotic transfer device that lifted the payload.

18. The method of claim 17, wherein positioning as well as aligning the rolling bed of the second autonomous robotic transfer device comprises:

computing a path for the rolling bed of the second autonomous robotic transfer device in terms of position as well as orientation; and driving the rolling bed of the second autonomous robotic transfer device along the said path.

\* \* \* \* \*